(12) United States Patent
Bussmann et al.

(10) Patent No.: US 7,652,048 B2
(45) Date of Patent: Jan. 26, 2010

(54) WATER-BASED, ANTIMICROBIALLY ACTIVE, DISPERSION CONCENTRATES

(75) Inventors: Werner Bussmann, Bad Nenndorf (DE); Burkhard Roessler, Neustadt (DE); Wolfgang Lindner, Parsippany, NJ (US)

(73) Assignee: Troy Corporation, Florham Park, NJ (US)

( * ) Notice: Subject to any disclaimer, the term of this patent is extended or adjusted under 35 U.S.C. 154(b) by 292 days.

(21) Appl. No.: 11/800,411

(22) Filed: May 4, 2007

(65) Prior Publication Data

US 2008/0274154 A1 Nov. 6, 2008

(51) Int. Cl.
A61K 31/425 (2006.01)

(52) U.S. Cl. .................................................. 514/373

(58) Field of Classification Search ................ 424/404, 424/405, 43, 70.1; 510/237, 433; 514/257
See application file for complete search history.

(56) References Cited

U.S. PATENT DOCUMENTS

| | | | |
|---|---|---|---|
| 3,726,970 | A | 4/1973 | Weisse |
| 4,923,887 | A | 5/1990 | Bauer et al. |
| 5,004,749 | A | 4/1991 | Jerusik et al. |
| 5,125,967 | A | 6/1992 | Morpeth et al. |
| 5,139,773 | A | 8/1992 | Tadros |
| 5,160,666 | A | 11/1992 | Lindner et al. |
| 5,252,321 | A | 10/1993 | Hth et al. |
| 6,306,413 | B1 | 10/2001 | Payne |
| 6,482,814 | B1 | 11/2002 | Bath et al. |
| 6,506,794 | B1 | 1/2003 | Sianawati et al. |
| 6,906,004 | B2 | 6/2005 | Parrish et al. |
| 7,105,555 | B2 | 9/2006 | Liu et al. |
| 2002/0164266 | A1 | 11/2002 | Wachtler et al. |
| 2004/0014799 | A1* | 1/2004 | Antoni-Zimmermann et al. ............... 514/372 |
| 2004/0224020 | A1 | 11/2004 | Schoenhard |
| 2004/0247626 | A1 | 12/2004 | Berg et al. |
| 2005/0065199 | A1* | 3/2005 | Beilfuss ....................... 514/372 |
| 2005/0209183 | A1 | 9/2005 | Kippenberger et al. |
| 2005/0261394 | A1 | 11/2005 | Branston et al. |
| 2006/0205716 | A1 | 9/2006 | Wachtler et al. |
| 2007/0031361 | A1 | 2/2007 | Herrmann et al. |
| 2007/0053944 | A1* | 3/2007 | Vermeer ..................... 424/405 |
| 2007/0092544 | A1 | 4/2007 | Mills |

FOREIGN PATENT DOCUMENTS

| | | |
|---|---|---|
| EP | 0224845 | 6/1987 |
| EP | 1 378 166 B1 | 12/2004 |
| EP | 07009024.6-1219 | 4/2008 |
| JP | 02-268900 | 11/1990 |
| WO | PCT/GB94/00100 | 8/1994 |
| WO | WO 00/35284 A | 6/2000 |
| WO | WO 00/60940 A | 10/2000 |
| WO | WO 02/19821 A | 3/2002 |
| WO | WO 2004/098289 A1 | 11/2004 |
| WO | WO 2008/142049 A1 | 5/2008 |

OTHER PUBLICATIONS

Uniqema Technical Bulletin 00-4 Atlox® Polymeric Surfactants: Agricultural Applicaitons—8 sheets downloaded from website www.uniqema.com on or about Apr. 11, 2007.
Uniqema Data for Atlox® 4913 Acrylic graft copolymer, 3 sheets downloaded from website www.uniqema.com on or about Feb. 1, 2007.
PCT/US 08/05154 Report, Jul. 25, 2008, PCT Search Report.
S. Haas et al. "Influence of polymeric sutfactants on pesticide suspension concentrates" Colloids and Surfaces No. 183-185, 2001 pp. 785-793 (cited by EPO in an international search report—see Cite No. S10 above).
WO 2008/142049 A1; PCT/EP2008/056119; 10, May 2008; Lanxess Deutschland GMBH 51369 Leverkusen (DE) 22 pages.

* cited by examiner

Primary Examiner—Johann R Richter
Assistant Examiner—Hong Yu
(74) Attorney, Agent, or Firm—Robert A. Yesukevich

(57) ABSTRACT

Highly concentrated, water-based dispersions of certain lipophilic and/or hydrophobic antimicrobially active materials are stabilized to a surprising degree by a surfactant combination including a nonionic acrylic graft copolymer surfactant and a alkoxylated polyarylphenol phosphate ester surfactant. The active materials may be present in dispersion concentrates of the present invention singly or in useful combinations. The active materials are selected from the group of fungicides and bactericides consisting of 1,2-benzisothiazol-3(2H)-one; 2-octyl-2H-isothiazol-3-one; 5-chloro-2-methyl-2H-isothiazol-3-one; 2-methyl-2H-isothiazol-3-one; pyrithione zinc; 3-iodo-2-propynyl butylcarbamate; 2-methylthio-4-ethylamino-6-tert-butylamino-s-triazine; and 3-(4-isopropylphenyl)-1,1-dimethylurea, and mixtures thereof. The dispersion concentrates may be efficiently shipped and stored, and subsequently diluted with water to produce less concentrated dispersions when desired. Even at relatively high concentrations, the dispersion compositions of the present invention can be stored for months or years without significant loss of stability.

32 Claims, No Drawings

WATER-BASED, ANTIMICROBIALLY ACTIVE, DISPERSION CONCENTRATES

BACKGROUND OF THE INVENTION

1. Field of the Invention

The present invention relates to compositions of matter which enhance the stability of solid-in-liquid dispersions. More specifically, the invention relates to surfactant systems for relatively lipophilic and/or hydrophobic materials, such as active antimicrobial materials, dispersed in lipophobic and/or hydrophilic liquids.

2. Description of Related Art

Water-based antimicrobial products are in great demand because, among other reasons, various governmental bodies have begun to restrict the use of solvents which contain volatile organic carbon (VOC). These restrictions are reportedly intended to enhance human health by improving the environment. As a result, many industries are switching from organic solvents to water-based solvents, which are inherently more susceptible to biological attack. More and better antimicrobial products are needed to protect the water-based solvents, and it is widely preferred that the antimicrobial products themselves are now also water-based and free of organic solvents.

To fulfill this need, concentrated products with relatively higher concentrations of antimicrobially active materials (hereinafter referred to as "actives") are favored by the antimicrobial product industry because concentrated products are easier to transport and store. However, many desirable actives are lipophilic and/or hydrophobic to the extent they do not easily dissolve in water-based liquids and are better combined in the form of solid-in liquid dispersions or liquid-in-liquid emulsions. Consequently, the physical stability of water-based dispersions containing active (hereinafter referred to as "active dispersions") is important.

Some otherwise desirable active dispersions are impractical because they exhibit phase separation over time. Other active dispersions simply cannot be prepared in the sought-after concentrations using currently available methods. This is frequently the case when a number of actives are combined in an attempt to formulate a single product which consumers may find more efficient and convenient to use, as compared to products having only one active. Concentrated water-based dispersions including a combination of actives are at the cutting edge of antimicrobial formulation development.

In order to meet the demand for concentrated water-based dispersions, some formulators have added pH-adjusting agents. Assuming that these pH-adjusting agents actually promote physical stability, they cannot be considered a final solution, because the change in pH which they bring about can negatively impact the performance of the actives.

U.S. Pat. No. 6,306,413, issued to Payne, describes a stable aqueous formulation comprising from 5 to 30% by weight microbiologically active agent containing at least 50% BIT, from 1 to 4% dispersant and from 0.1 to 0.5% by weight xanthan gum. The formulation is said to be substantially free from organic solvents. Dispersants of the '413 patent reportedly include condensates of ethylene oxide or propylene oxide (including block co-polymers of ethylene oxide and propylene oxide), sodium lignin sulphonate, the sodium salt of naphthalene sulphonic acid/formaldehyde condensates and mixtures thereof. However, as demonstrated below, the present inventors have found that the sodium lignin sulphonate-containing formulations of the '413 patent exhibit undesirably high viscosities at relatively higher concentrations.

Japanese unexamined application JP 2-268900, assigned to Kurita Seisakusho K.K. and Kurita Water Industries Ltd., describes a slurry-form deodorizing agent for use in preventing foul smells arising from sludge. The deodorizing agent of the '900 application reportedly comprises 5-70 wt % of a deodorant such as 1,2-benzisothiazol-3(2H)-one or methylene bis-thiocyanate, 0.1-10 wt % xanthan gum, 0.1-0.5 wt % polyacrylamide which optionally may be partially hydrolyzed, and water. However, as demonstrated below, the polyacrylamide-containing formulations of the '900 patent exhibit undesirably high viscosities at relatively higher concentrations.

World Intellectual Property Organization patent application no. PCT/EP04/10114, assigned to Bayer CropScience LP, describes suspension concentrates comprising a) at least one active compound, solid at room temperature, from the group of the azoles and/or the strobilurins, b) at least one penetration enhancer from the group of the alkanolethoxylates, c) at least one dispersant from the group of the polymers of methyl 2-methyl-2-propenoate and alpha-(2-methyl-1-oxo-2-propenyl)-omega-methoxypoly-(oxy-1,2-ethanediyl), the tristyrylphenolethoxylates and/or the propylene oxide/ethylene oxide block copolymers having molecular weights between 8000 and 10 000, d) water and also e) additives, if appropriate. However, the alkanolethoxylates required by the '114 application are organic solvents and, therefore, inappropriate for use in organic solvent free, water-based antimicrobial products.

Previous researchers have devoted much effort to developing better surfactant systems and improved antimicrobial formulations. However, a need still exists for a surfactant system which stabilizes relatively concentrated, water-based dispersions of combined actives over a practical viscosity range and at a pH which is approximately neutral. New dispersions which include the surfactant system should be essentially free of organic solvents, should be effective for a number of proven active antimicrobial materials, and should not discolor other products to which they may be added or applied.

SUMMARY OF THE INVENTION

It has now been discovered that water-based dispersion compositions which include certain lipophilic and/or hydrophobic antimicrobially active materials in a dispersed phase, an acrylic graft copolymer surfactant, and an ionic alkoxylated polyarylphenol phosphate ester surfactant are stable over time at surprisingly high concentrations of the active materials. The active materials may be present in dispersion concentrates of the present invention singly or in useful combinations. The dispersion concentrates may be efficiently shipped and stored, and subsequently diluted with water to produce less concentrated dispersions when desired.

In a preferred aspect, the invention is a dispersion composition which includes about 5 to about 60 mass percent of a selected antimicrobially active material in a dispersed phase. The active material is selected from the group of fungicides and bactericides consisting of 1,2-benzisothiazol-3(2H)-one; 2-octyl-2H-isothiazol-3-one; 5-chloro-2-methyl-2H-isothiazol-3-one; 2-methyl-2H-isothiazol-3-one; pyrithione zinc; 3-iodo-2-propynyl butylcarbamate; 2-methylthio-4-ethylamino-6-tert-butylamino-s-triazine; and 3-(4-isopropylphenyl)-1,1-dimethylurea, and mixtures thereof.

The dispersion composition also includes about 0.1 to about 5 mass percent of an acrylic graft copolymer having a poly(methyl methacrylate-methacrylic acid) backbone and polyethylene glycol side chains, and about 0.1 to about 5 mass percent of a tristyrylphenolethoxylate phosphoric ester or a salt thereof having an average of about 50 to about 60 ethylene oxide units. Preferably the acrylic graft copolymer is a copolymer of methyl 2-methyl-2-propenoate and alpha-(2-methyl-1-oxo-2-propenyl)-omega-methoxypoly-(oxy-1,2-ethanediyl).

Preferably, the dispersion composition includes about 30 to about 60 mass percent of the active material, more preferably about 45 to about 55 mass percent of the active material. Even at these relatively high concentrations, the dispersion compositions of the present invention can be stored for months or years without significant loss of stability.

The active materials are present as solid or liquid particles dispersed in a continuous phase of water-based solvent. The particles are preferably about forty microns or less in size, more preferably about fifteen microns or less. Preferably, the water-based solvent includes essentially no VOC and essentially no organic solvent. More preferably, the water-based solvent consists essentially of water, an optional defoamer, and an optional viscosity modifier.

In another preferred aspect, the invention is a water-based dispersion concentrate which includes at least about 35 mass percent BIT, tristyrylphenolethoxylate phosphoric ester or a salt or acid form thereof; and an acrylic graft copolymer. The dispersion concentrate exhibits no significant phase separation or change in viscosity at about 20° C. over a period of at least about twelve months.

In yet another preferred aspect, the invention is a water-based dispersion concentrate which includes at least about 45 mass percent OIT, ZPT, IPBC, TERT, IPU or mixtures thereof; a tristyrylphenolethoxylate phosphoric ester or a salt or acid form thereof; and an acrylic graft copolymer. The dispersion concentrate exhibits no significant phase separation or change in viscosity at about 40° C. over a period of at least about two months.

In still another preferred aspect, the invention is a microbial biocide produced by diluting a dispersion concentrate of the present invention.

DETAILED DESCRIPTION OF PREFERRED EMBODIMENTS

In a preferred embodiment, the invention is a water-based dispersion composition, which includes a solid-in-liquid dispersions or a liquid-in-liquid dispersion. The dispersion composition includes a nonionic polymeric surfactant. Preferably, the polymeric surfactant is an acrylic graft copolymer having a poly(methyl methacrylate-methacrylic acid) backbone and polyethylene oxide side chains. More preferably, the acrylic graft copolymer is a copolymer of methyl 2-methyl-2-propenoate and alpha-(2-methyl-1-oxo-2-propenyl)-omega-methoxypoly-(oxy-1,2-ethanediyl). One especially preferred acrylic graft polymer is commercially available from Crodia International of Cowick Hall, Yorkshire, England (previously Uniqema) under the tradename Atlox 4913.

The dispersion composition additionally includes an ionic surfactant, which is an alkoxylated polyarylphenol phosphate ester (or a salt or an acid form thereof). For example, the ionic surfactant may enter the water-based solvent in the form of a sodium, an ammonium or a potassium salt, and subsequently dissociate in the course of dissolving. Tristyrylphenolethoxylate phosphate ester and its salt and acid forms are preferred. The potassium salt of tristyrylphenolethoxylate phosphate ester (hereinafter referred to as "TSPPE"), which is commercially available from Rhodia, Inc. under the tradename Soprophor FLK, is especially preferred.

Examples of relatively water-insoluble antimicrobially active materials which are useful as bactericides, fungicides or algaecides in the present invention include: 1,2-benzisothiazol-3(2H)-one (BIT); 2-octyl-2H-isothiazol-3-one (OIT); 2-methyl-2H-5-chloro-2-methyl-2H-isothiazol-3-one (CIT); and isothiazol-3-one (MIT); pyrithione zinc (ZPT); 3-iodo-2-propynyl butylcarbamate (IPBC); 2-methylthio-4-ethylamino-6-tert-butylamino-s-triazine (TERB); and 3-(4-isopropylphenyl)-1,1-dimethylurea (IPU). Further, the following are possible examples for the use of the invention: Carbendazim (BCM), Dichloroctylisothiazolinone (DCOIT), Thiabendazole (TBZ), Cybutryn, Diuron, Dazomet, Chloracetamide, Tebuconazole, ortho-phenylphenol (OPP).

For the present purposes, "microbe" means a minute life form such as, for example, a bacterium, fungus, mushroom, mold, smut, rust, or yeast. "Antimicrobially active material" means a material that is known to terminate or retard the growth of at least a certain class of microbes, when the microbes are exposed to the material in amounts which are harmless to humans.

The antimicrobially active material is present as solid or liquid particles dispersed in a continuous phase of water-based solvent. The particles are preferably about forty microns or less in size, more preferably about fifteen microns or less. This particle size range can be achieved through milling of the particles by conventional techniques. Typically, the particles are mechanically milled at room temperature in the presence of water, the polymeric surfactant and the ionic surfactant. The milling can be aided by the use of inert filler materials, such as china clay.

Dispersions of the selected active materials are miscible amongst themselves. For example, the BIT dispersion of the present invention can be combined easily with the OIT dispersion of the present invention, and no loss in stability results. The resulting combination mixture can be diluted and brought back to original viscosity by the addition of the appropriate amount of a viscosity modifier (which may be, for example, Kelzan or xanthan gum). Preferably, the original viscosity or the modified viscosity is at least about 2000 mPa-s and less than about 5000 mPa-s. Preferably, the viscosity modifier is xanthan gum in the amount of about 0.05 to about 2 mass percent, more preferably about 0.5 to about 1.5 mass percent.

It is expected and encouraged that formulators will employ the dispersion compositions of the present invention, directly or after dilution, singly or in combination, to produce microbial biocides for disinfecting or protecting a variety of substrates. Examples of suitable substrates include in-can or dry-film coatings, adhesives, textiles, sealants, polymers emulsions, plastics, construction products, art materials, paints and varnishes, among others.

Preferably, the water-based solvent includes essentially no VOC and essentially no organic solvent. More preferably, the water-based solvent consists essentially of water, an optional defoamer, and an optional viscosity modifier. However, it is contemplated that conventional adjuvants may be included in the dispersion compositions of the present invention in order to satisfy the preferences or applications of particular users.

Some of the conventional adjuvants which may be utilized in the invention are pH-adjusting or buffering agents, preservatives, perfumes, deodorizers, colorants, dyes, defoamers, antioxidants, and additional surfactants, such as ethylene/propylene block polymers.

"Includes essentially no" means that the material so described is not present in the composition of interest, or is present in an amount that has at most an insignificant effect on the macroscopic properties of the composition of interest. "Optional" means that he material so described may be present but is not required.

The following examples are presented to better communicate the invention, and are not intended to limit the invention in any way.

EXAMPLE 1

51% BIT, 1.5% TSPPE, 1.5% Graft Polymer

The formulation is prepared by mixing 73 parts by mass of BIT wet cake (70% active material) in 15 parts of water with the use of a dissolver apparatus (Dispermat of VMA Getzmann GmbH) operated from 500 to 2500 rpm. Under continued mixing, 1.5 parts of the potassium salt of tristyrylphenolethoxylate phosphate ester (TSPPE), 1.5 parts of an acrylic graft copolymer are added together with 0.1 part of a silicon-based defoamer. The potassium salt employed was commercially obtained from Degussa under the tradename Soprophor FLK. The acrylic graft polymer was commercially obtained from Crodia International under the tradename Atlox 4913. The defoamer was commercially obtained from Rhodia, Inc. under the tradename Rhodorsil Antifoam 416. The mixture was milled with 1.2 mm zirconium-beads in the dissolver apparatus to a maximum particle size of 15 microns. The viscosity of the milled mixture was increased to about 2500 mPa-s by adding 0.2 parts of xanthan gum in the dissolver apparatus to produce the dispersion of Example 1. The dispersion was stored at 20° C. for twelve months, during which time the viscosity of the dispersion was periodically measured. No significant change in the viscosity of the dispersion was observed. The results are shown below in Table 1.

EXAMPLE 2

50% Active, 1.65% TSPPE, 1.65% Graft Polymer

The procedure described above in Example 1 was repeated with the materials and amounts listed below for actives OIT, ZPT, IPBC, TERB and IPU. Each of the dispersions 2a through 2e was stored at 40° C. for two months, during which time the viscosity of the dispersion was periodically measured. No significant change in the viscosity of any of the dispersions 2a through 2e was observed. The results are shown below in Table 1.

TABLE I

| Example No. | Active Name* | Active mass % | TSPPE mass % | Graft Polymer mass % | Defoamer mass % | Xanthan Gum mass % | Water mass % | Viscosity + mPa-s |
|---|---|---|---|---|---|---|---|---|
| 1 | BIT | 51 | 1.5 | 1.5 | 0.1 | 0.2 | 45.7 | 2500 |
| 2a | OIT | 50 | 1.65 | 1.65 | 0.1 | 0.3 | 46.3 | 4000 # |
| 2b | ZPT | 50 | 1.65 | 1.65 | 0.1 | 0.2 | 46.4 | 2000 |
| 2c | IPBC | 50 | 1.65 | 1.65 | 0.1 | 0.2 | 46.4 | 2400 |
| 2d | TERB | 50 | 1.65 | 1.65 | 0.1 | 0.2 | 46.4 | 2800 |
| 2e | IPU | 50 | 1.65 | 1.65 | 0.1 | 0.2 | 46.4 | 2600 |

Note *
1,2-benzisothiazol-3(2H)-one (BIT); 2-octyl-2H-isothiazol-3-one (OIT); pyrithione zinc (ZPT); 3-iodo-2-propynyl butylcarbamate (IPBC); 2-methylthio-4-ethylamino-6-tert-butylamino-s-triazine (TERB); and 3-(4-isopropylphenyl)-1,1-dimethylurea (IPU)
Note +
Viscosities were measured at 10 rpm with spindle No. 4 in a Brookfield viscometer.
Note #
The relatively large viscosity of 4000 is believed to be due to the relatively greater amount of xanthan gum added to Example 1, as compared to Examples 1 and 2b through 2e.

EXAMPLE 3

25% BIT, 5% OIT, 0.92% TSPPE, 0.92 Graft Polymer 50 parts of a dispersion identical to the dispersion of Example 1 and 10 parts of a dispersion identical to the dispersion of Example 2a was mixed in the dissolver apparatus, as described in Example 1. Water was added to make up 100 parts. The viscosity of the dispersion was measured as approximately 2000 mPa. The results are shown Table II.

EXAMPLE 4

10.8% BIT, 0.5% CIT, 0.2% MIT, 0.92% TSPPE, 0.92 Graft Polymer 20 parts of a dispersion identical to the dispersion of Example 1 were combined with 74.6 parts of an aqueous solution of 5-chloro-2-methyl-2H-isothiazol-3-one (CIT) and 2-methyl-2H-isothiazol-3-one (MIT) to produce a dispersion including a total of 10.8 mass % BIT, 0.5 mass % CIT and 0.2 mass % MIT. The measured viscosity was adjusted with 0.4 parts of xanthan gum to approximately 1800 mPa. The resulting formulation exhibited excellent stability for two months at 40° C. The results are shown Table II.

TABLE II

| Example No. | Active Name = | Active mass % | TSPPE mass % | Graft Polymer mass % | Defoamer mass % | Xanthan Gum mass % | Water mass % | Viscosity mPa-s |
|---|---|---|---|---|---|---|---|---|
| 3 | BIT | 25 | 0.92 | 0.92 | 0.50 | 0.32 | 67.4 | 2000 |
|   | OIT | 5 |   |   |   |   |   |   |
| 4 | BIT | 10.8 | 0.3 | 0.3 | 0.02 | 0.44 | 87.4 | 1800 |
|   | CIT | 0.5 |   |   |   |   |   |   |
|   | MIT | 0.2 |   |   |   |   |   |   |

Note =
1,2-benzisothiazol-3(2H)-one (BIT); 2-octyl-2H-isothiazol-3-one (OIT); 2-methyl-2H-5-chloro-2-methyl-2H-isothiazol-3-one (CIT); and isothiazol-3-one (MIT)

COMPARATIVE EXAMPLE A

An attempt was made to again perform the procedure described above in Example 1, except that an amount of lignin sulfonates corresponding to 7.5 mass % of the total composition was added in place of 1.5 parts of TSPPE and 5.5 parts of the acrylic graft copolymer. The mixture which resulted exhibited an exceedingly high viscosity which prevented milling in the Dispermat apparatus. Consequently, the attempt was abandoned.

EXAMPLE B

For Comparison

An attempt was made to again perform the procedure described above in Example 1, except that an amount of polyacrylamide corresponding to 0.5 mass % of the total composition was added in place of 1.5 parts of TSPPE and 5.5 parts of the acrylic graft copolymer. The mixture which resulted exhibited an exceedingly high viscosity which prevented milling in the Dispermat apparatus. Consequently, the attempt was abandoned.

EXAMPLE 5

25% BIT, 25% OIT, 0.92% TSPPE, 0.92 Graft Polymer

Dispersions identical to those described above in Examples 1 and 2a were mixed in a ratio of one part to one part to produce a dispersion including a combination of actives, which exhibited good stability and viscosity similar to that of the initial dispersions. Results are shown below in Table III.

EXAMPLE 6

25% TERB, 25% IPBC, 0.92% TSPPE, 0.92 Graft Polymer

Dispersions identical to those described above in Examples 2d and 2c were mixed in a ratio of one part to one part to produce a dispersion including a combination of actives, which exhibited good stability and viscosity similar to that of the initial dispersions. Results are shown below in Table III.

EXAMPLE 7

25% TERB, 25% IPBC, 0.92% TSPPE, 0.92 Graft Polymer

Dispersions identical to those described above in Examples 2d and 2e were mixed in a ratio of one part to one part to produce a dispersion including a combination of actives, which exhibited good stability and viscosity similar to that of the initial dispersions. Results are shown below in Table III.

TABLE III

| Example No. | Active Name ~ | Active mass % | TSPPE mass % | Graft Polymer mass % | Defoamer mass % | Xanthan Gum mass % | Water mass % | Viscosity + mPa-s |
|---|---|---|---|---|---|---|---|---|
| 5 | BIT from Ex. 1 | 25.5 | 1.58 | 1.58 | 0.1 | 0.25 | 46.0 | 4500 |
|   | OIT from Ex. 2a | 25 |   |   |   |   |   |   |
| 6 | TERB from Ex. 2d | 25 | 1.65 | 1.65 | 0.1 | 0.2 | 46.4 | 2500 |
|   | IPBC from Ex 2c | 25 |   |   |   |   |   |   |

TABLE III-continued

| Example No. | Active Name ~ | Active mass % | TSPPE mass % | Graft Polymer mass % | Defoamer mass % | Xanthan Gum mass % | Water mass % | Viscosity + mPa·s |
|---|---|---|---|---|---|---|---|---|
| 7 | TERB from Ex. 2d | 25 | 1.65 | 1.65 | 0.1 | 0.2 | 46.4 | 2400 |
|   | IPU from Ex. 2e | 25 |   |   |   |   |   |   |

Note ~
1,2-benzisothiazol-3(2H)-one (BIT); 2-octyl-2H-isothiazol-3-one (OIT); 3-iodo-2-propynyl butylcarbamate (IPBC); 2-methylthio-4-ethylamino-6-tert-butylamino-s-triazine (TERB); and 3-(4-isopropylphenyl)-1,1-dimethylurea (IPU)
Note +
Viscosities were measured at 10 rpm with spindle No. 4 in a Brookfield viscometer.

The Examples set forth above are not intended to limit the invention in any way. The invention is defined solely by the appended claims.

We claim as our invention:

1. A dispersion composition, which comprises:
   about 5 to about 60 mass percent of an antimicrobially active material selected from the group consisting of 1,2-benzisothiazol-3(2H)-one; 2-octyl-2H-isothiazol-3-one; pyrithione zinc; 3-iodo-2-propynyl butylcarbamate; 2-methylthio-4-ethylamino-6-tert-butylamino-s-triazine; and 3-(4-isopropylphenyl)-1,1-dimethylurea, and mixtures thereof;
   about 0.1 to about 5 mass percent of an acrylic graft copolymer having a poly(methyl methacrylate-methacrylic acid) backbone and polyethylene glycol side chains;
   about 0.1 to about 5 mass percent of a tristyrylphenolethoxylate phosphoric ester or a salt or acid form thereof, having an average of about 50 to about 60 ethylene oxide units; and
   a water-based solvent.

2. The composition of claim 1 in which the acrylic graft copolymer is a copolymer of methyl 2-methyl-2-propenoate and alpha-(2-methyl-1-oxo-2-propenyl)-omega-methoxypoly-(oxy-1,2-ethanediyl).

3. The composition of claim 1 which includes about 30 to about 60 mass percent of the antimicrobially active material.

4. The composition of claim 3 which includes about 45 to about 55 mass percent of the antimicrobially active material.

5. The composition of claim 1 in which the water-based solvent consists essentially of water, an optional defoamer, and an optional viscosity modifier.

6. The composition of claim 1 which includes essentially no volatile organic carbon.

7. The composition of claim 1 which includes essentially no organic solvent.

8. The composition of claim 1 which includes a viscosity modifier.

9. The composition of claim 8 in which the viscosity modifier is xanthan gum in the amount of about 0.05 to about 2 mass percent.

10. The composition of claim 1 in which the antimicrobially active material includes 1,2-benzisothiazol-3(2H)-one.

11. The composition of claim 1 in which the antimicrobially active material includes 5-chloro-2-methyl-2H-isothiazol-3-one; 2-methyl-2H-isothiazol-3-one.

12. The composition of claim 1 in which the antimicrobially active material includes 2-methyl-2H-isothiazol-3-one.

13. The composition of claim 1 in which the antimicrobially active material includes 2-octyl-2H-isothiazol-3-one.

14. The composition of claim 1 in which the antimicrobially active material includes pyrithione zinc.

15. The composition of claim 1 in which the antimicrobially active material includes 3-iodo-2-propynyl butylcarbamate.

16. The composition of claim 1 in which the antimicrobially active material includes 3-(4-isopropylphenyl)-1,1-dimethylurea.

17. The composition of claim 1 which has a viscosity of at least about 2000 mPa·s.

18. The composition of claim 1 which has a viscosity of less than about 5000 mPa·s.

19. The composition of claim 1 which includes
   about 10 mass percent 1,2-benzisothiazol-3(2H)-one;
   about 0.5 mass percent 5-chloro-2-methyl-2H-isothiazol-3-one; and
   about 0.2 mass percent 2-methyl-2H-isothiazol-3-one, based on the total mass of the composition.

20. A microbial biocide produced by diluting the composition of claim 1.

21. A dispersion composition, which comprises:
   at least about 35 mass percent 1,2-benzisothiazol-3(2H)-one;
   an acrylic graft copolymer;
   a tristyrylphenolethoxylate phosphoric ester or a salt or acid form thereof; and
   water;
   wherein the composition is stable at about 20° C. for at least about twelve months.

22. A dispersion composition, which comprises:
   at least about 45 mass percent of an antimicrobially active material selected from the group consisting of 2-octyl-2H-isothiazol-3-one; pyrithione zinc; 3-iodo-2-propynyl butylcarbamate; 2-methylthio-4-ethylamino-6-tert-butylamino-s-triazine; and 3-(4-isopropylphenyl)-1,1-dimethylurea, and mixtures thereof;
   an acrylic graft copolymer;
   a tristyrylphenolethoxylate phosphoric ester or a salt or an acid form thereof; and
   water;
   wherein the composition is stable at about 40° C. for at least about two months.

23. A dispersion composition for disinfecting or protecting in-can or dry-film coatings, adhesives, textiles, sealants, polymers emulsions, plastics, construction products, art materials, paints and varnishes, which comprises:
   about 45 to about 60 mass percent of an antimicrobially active material which is 3-iodo-2-propynyl butylcarbamate;

about 0.1 to about 5 mass percent of an acrylic graft copolymer having a poly(methyl methacrylate-methacrylic acid) backbone and polyethylene glycol side chains;

about 0.1 to about 5 mass percent of a tristyrylphenolethoxylate phosphoric ester or a salt or acid form thereof, having an average of about 50 to about 60 ethylene oxide units; and a water-based solvent;

which dispersion composition has a viscosity of less than about 5000 mPa-s.

24. The composition of claim 23 in which the acrylic graft copolymer is a copolymer of methyl 2-methyl-2-propenoate and alpha-(2-methyl-1-oxo-2-propenyl)-omega-methoxy-poly-(oxy-1,2-ethanediyl).

25. The composition of claim 23 in which the water-based solvent consists essentially of water, an optional defoamer, and an optional viscosity modifier.

26. The composition of claim 23 which includes essentially no volatile organic carbon.

27. The composition of claim 23 which includes essentially no organic solvent.

28. The composition of claim 23 which includes a viscosity modifier.

29. The composition of claim 28 in which the viscosity modifier is xanthan gum in the amount of about 0.05 to about 2 mass percent.

30. The composition of claim 23 which has a viscosity of at least about 2000 mPa-s.

31. A microbial biocide produced by diluting the composition of claim 23.

32. A dispersion composition, which comprises:

about 45 to about 60 mass percent of an antimicrobially active material which is 3-iodo-2-propynyl butylcarbamate;

an acrylic graft copolymer;

a tristyrylphenolethoxylate phosphoric ester or a salt or an acid form thereof; and water;

wherein the dispersion composition has a viscosity of less than about 5000 mPa-s; and wherein the dispersion composition is stable at about 40° C. for at least about two months.

* * * * *